United States Patent [19]
Hall

[11] 4,201,051
[45] May 6, 1980

[54] PRESSURIZED FLUID CONTROL CIRCUIT

[76] Inventor: Arthur L. Hall, 520 Bardon Rd., Knoxville, Tenn. 37919

[21] Appl. No.: 965,787

[22] Filed: Dec. 4, 1978

Related U.S. Application Data

[63] Continuation-in-part of Ser. No. 722,609, Sep. 13, 1976, Pat. No. 4,145,813.

[51] Int. Cl.² ............................................. F15B 11/06
[52] U.S. Cl. ...................................... 60/407; 60/484; 433/101
[58] Field of Search ................. 60/407, 412, 458, 484, 60/DIG. 10; 32/22

[56] References Cited

U.S. PATENT DOCUMENTS

| | | | |
|---|---|---|---|
| 3,511,264 | 5/1970 | Krantz | 32/22 X |
| 3,718,973 | 3/1973 | Slater et al. | 32/22 |
| 3,886,660 | 6/1975 | Thornton et al. | 32/22 |
| 4,063,627 | 12/1977 | Wright | 60/407 X |

Primary Examiner—Edgar W. Geoghegan
Attorney, Agent, or Firm—Luedeka & Hodges

[57] ABSTRACT

A system for selectively and controllably supplying pressurized fluids to dental or surgical tools requiring high pressure air at two levels of pressure and low pressure air and/or liquid.

5 Claims, 14 Drawing Figures

PRESSURIZED FLUID CONTROL CIRCUIT

This is a continuation-in-part of my application Ser. No. 722,609, filed Sept. 13, 1976, issued as U.S. Pat. No. 4,145,813 on Mar. 27, 1979.

The present invention relates generally to improvements in the provision of dental and surgical equipment and more particularly to an improved apparatus for control of pressurized fluid flow to dental and surgical tools. The present invention has particular application to systems for controlling a plurality of tools, each of which requires supplies of a plurality of pressurized fluids and at least one of which tools require drive gas at a pressure substantially greater than the pressure of gas supplied to the other tools.

In fields of dentistry and surgery a variety of hand tools are used, many of which require several pressurized fluids. For example, drills and other cutting tools are generally driven by gas turbines which are powered by a supply of pressurized gas, called drive gas. Drive gas may comprise compressed air or bottled nitrogen, for example. In addition, many operations require pressurized gas and/or a liquid, such as water or saline solution, for cooling and/or clearing the working area.

Usually, an operator will maintain several tools in a "ready" condition, either in case a bit breaks or to perform different procedures without changing bits.

Also, there are different types of drills which require drive gas at differing pressures. For example, the typical dental drill which operates at high speed and relatively low torque is powered by gas at a pressure of about 30-35 psig. Surgical drills, however, which operate at lower speeds and high torque, are commonly powered by gas at pressures of about 90 psig and as high as 150 psig.

Conventionally, control means are provided to perform the functions of receiving pressurized gas and liquid from their respective sources, splitting the gas for use in various functions, and selectively supplying the fluids to a series of valves. (Usually, each tool has an individual valve associated with it.) When the operator selects the appropriate tool and required fluids for a particular procedure, he sets the control mechanism to supply the desired fluids and actuates the associated valve to permit the fluids to flow to the tool. The rate of flow of the drive gas is controlled by the operator with either a control on the drill itself or a foot pedal, so that his hands are free to handle tools.

A variety of prior art apparatus have been used as control mechanisms. However, there have also been a variety of attendant deficiencies.

The known controls for apparatus of the class described have generally required separate systems to supply fluids to such varying tools. Essentially, in most of the prior art devices, the control of fluids has been effected by a multiplicity of diaphragm valves which are incorporated in the control. Diaphragm valves are not entirely satisfactory at high pressures and particularly at a pressure as high as 150 psi, which is required for some of the more modern surgical type tools. Breakdown of a valve or valves can make the entire control system inoperable. Repair, when the valve is incorporated with a member of other valves and elements in the system, is both time consuming and expensive. This has resulted in a substantial amount of "down time" and relatively high maintenance costs. In my prior application, Ser. No. 722,609, I have described and claimed a control system which eliminates various of the problems which occurred in prior systems.

It has also been necessary to provide separate control systems for surgical tools which are powered by drive gas at substantially elevated pressures. Separate systems are particularly undesirable in the area of surgery because the operator requires ready access to the control system and flexibility in his choice of tools, yet space is at a premium in an operating room.

The principal object of this invention is to provide a single fluid system, which can be used for a variety of types of dental and surgical tools requiring substantially different gas pressures without unnecessary reinforcement of the entire system. A further object of the invention is to provide a unit in which the valve set for any tool can be quickly, and economically replaced by the operator without the need of a trained serviceman.

Other objects and advantages of the invention will become apparent by reference to the following description and the accompanying drawings.

Figure 1:
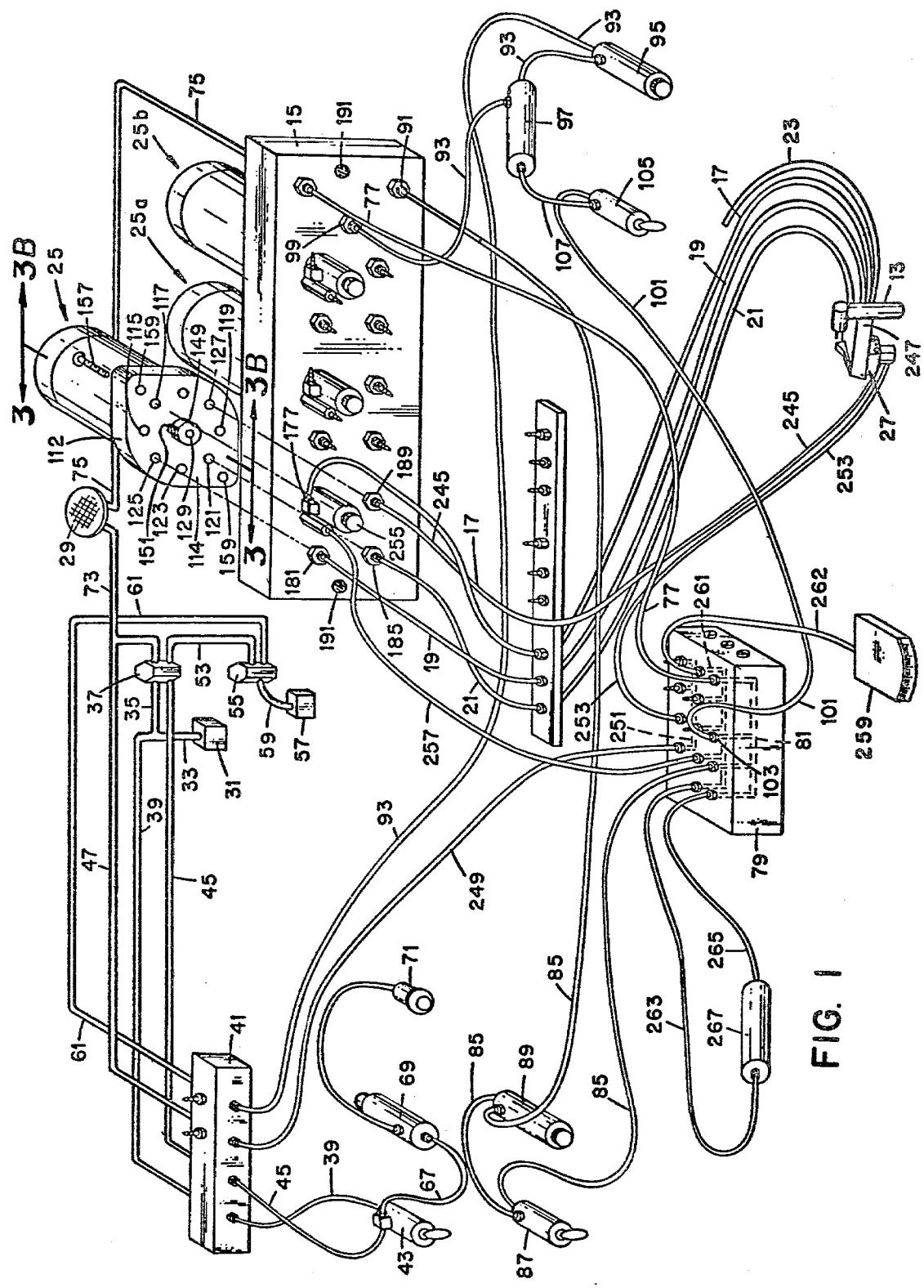
FIG. 1 is a diagrammatic view of a tool system and control means for controlling three tools requiring fluids at similar pressures.

The systems illustrated in the drawings are adapted to operate dental and surgical tools from a single source of pressurized gas. The gas may comprise compressed air. However, in most surgical settings nitrogen is used as a safety measure to prevent fires and explosives. Tools of this type are driven by gas turbines within the tool and include such tools as drills, and the like. Such tools, also generally include means for dispensing a liquid, such as water or saline solution, to cool and lubricate the work area and also usually include means for dispensing gas at low pressure which is used for various purposes such as cooling the work area, drying the work area, or clearing the area of chips. This low pressure gas will be referred to hereinafter as "chip gas."

Drive gas is conducted to the tools at pressures which range from 30–150 pounds psig, depending upon the type of tool being supplied and the particular speed of rotation which is desired for that tool. To this end, controls are provided for selecting and adjusting the drive gas pressure for individual tools. Means are also provided in the system for selectively applying chip gas and/or liquid depending upon the working conditions.

Figure 2:
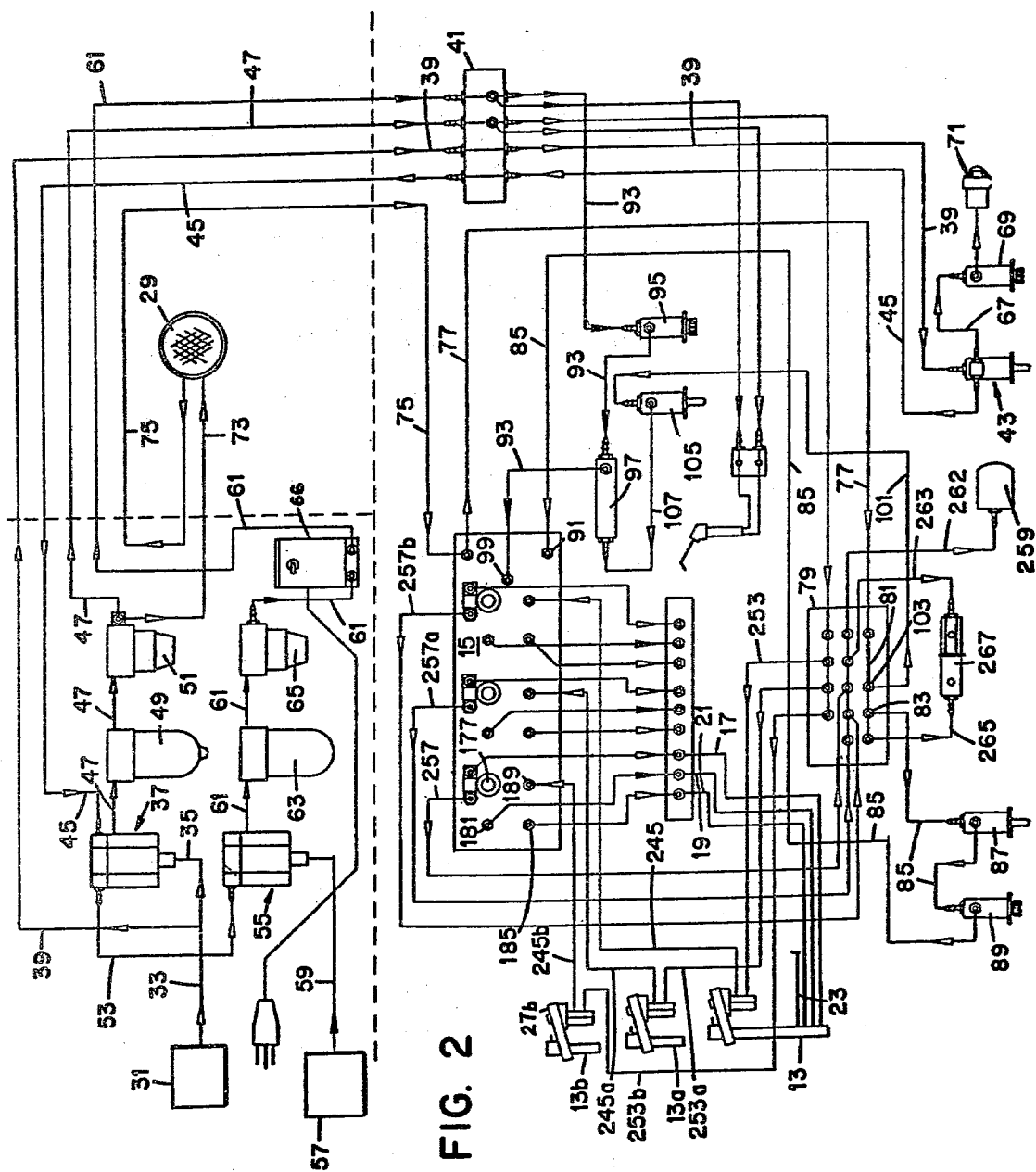
FIG. 2 is a schematic flow diagram of a control system for controlling three separate tools.
Figure 4:
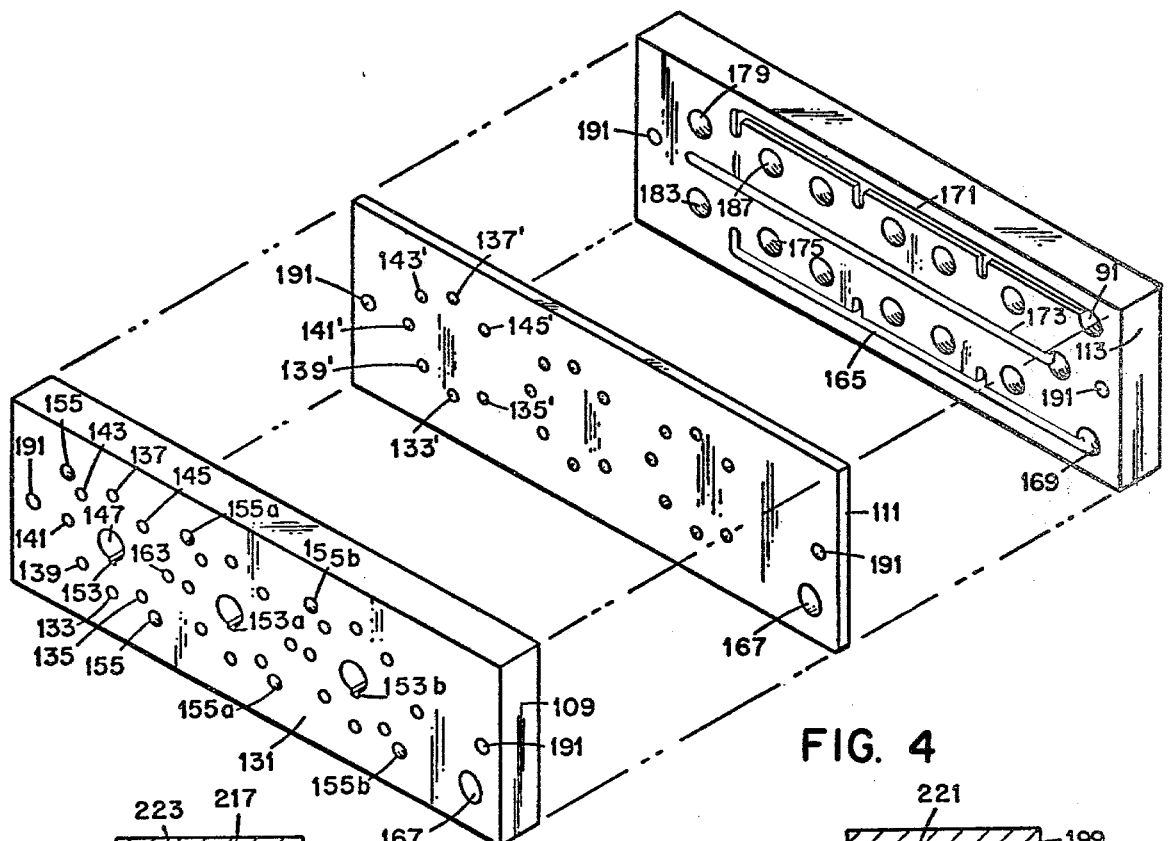
FIG. 4 is an exploded perspective view of the manifold which is a part of the control means shown in FIG. 1.

In FIGS. 1 and 2 there is illustrated a system for supplying a set of three equivalent air turbine drills, 13, 13a, and 13b. In order to simplify the description, only the connections for one drill 13 will be described in detail, it being understood that the other drills 13a and 13b are connected in the same manner with the corresponding elements being identified with the same reference numbers carrying the suffix "a" or "b", respectively. Drill 13 is connected to a manifold 15 by three conduits, 17, 19, and 21, conduit 17 being adapted to supply drive air, conduit 19 being adapted to provide liquid, and conduit 21 being adapted to provide chip air. A fourth conduit 23 extends from the tool to exhaust the spent drive air from the drill 13 to a point remote from that at which the work is taking place. The manifold 15 shown in FIG. 1 is designed to accommodate three separate tools and it is within the scope of this invention to provide manifolds which accommodate any desired number of tools.

Briefly, the manifold 15 is supplied with drive air, chip air and liquid at working pressures. Control of the flow of fluids from the manifold 15 is accomplished by individually replaceable valve sets 25, 25a and 25b, which are removably attached to the manifold 15, one valve set being provided for each tool. In operation, each valve set is actuated by a source of pressure air to simultaneously supply the desired combination of drive air, chip air and liquid to its associated tool.

Actuation of any given tool is accomplished by removing the tool from its associated hanger or rest 27, 27a or 27b which readies the fluid supply to its associated tool. Activation of the tool is then accomplished through a foot pedal actuated valve 29 or other activation device. Individual manually actuated controls are provided to supply chip air and/or liquid, as desired.

The system is connected to a suitable source of pressure air 31 through conduit 33. The pressure in the source is selected to be higher than the highest pressure to be supplied to the tools, taking into account the pressure drop which occurs in the system between the source of air and the tools. The conduit 33 is connected through conduit 35 to the inlet of an air actuated, normally closed control valve 37 and through conduit 39 and through a junction block 41 to a manually actuated master valve 43. When the master valve 43 is manually opened, it supplies air through conduit 45 through the junction block 41 and through conduit 45 to the air operated valve 37 which is thus opened connecting the source of air 31 through conduit 47 to the junction block 41. In the conduit 47, there are provided a suitable filter 49 to remove any undesirable suspended material and a regulator 51 to control the pressure of air supplied to the system.

The pressurized air from the conduit 45 which is utilized to actuate the valve 37 is conducted through conduit 53 to an air actuated, normally closed, water valve 55. The inlet of the water valve 55 is connected to a source of pressurized water 57 through the conduit 59 and the outlet of the valve 55 is connected through conduit 61 to the junction block 41. In the conduit 61 there are provided a suitable filter 63 to remove any undesirable foreign materials from the liquid, a regulator 65 to control the pressure of water supplied to the system, and an electrical heater 66 which is employed to heat the liquid to the desired temperature.

In order that there is an indicator to show whether or not the unit is being supplied with pressurized air and water, the outlet of the master valve 43 is also connected by conduit 67 through a pressure reducer 69 to an air actuated indicator light 71.

In order to provide drive air to the manifold 15, a conduit 73 interconnects the foot pedal actuated valve 29 to the conduit 47. The valve 29 is in turn connected to the manifold 15 by means of conduit 75.

In order to supply water to the manifold, the conduit 61 at the junction block 41 is connected by means of a conduit 93 including a pressure regulator 95 and an air actuated valve 97 to the water inlet 99 on the manifold 15. Control of the supply of water is effected by the air actuated valve 97. This control is effected by air from an air conduit 101, having one end connected to an outlet 103 in the distributor block which in turn communicates with the air passageway 81. The other end of the conduit 101 is connected to the inlet of a manually actuated air valve 105 whose outlet communicates with the air inlet on the control valve 97 through conduit 107.

The manifold 15 serves as a mounting surface for the valves 25, 25a and 25b and as conduit means to and from the valves 25, 25a and 25b for water, chip air, drive air and pilot air (also called "control air" because it is used to control the valves). The manifold 15 is essentially a unitary block formed by three sealably joined sections, a mounting section 109, a middle section 111, and a face section 113.

Figure 11:
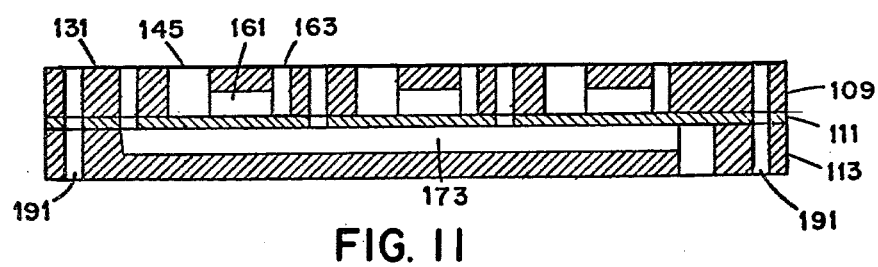
FIG. 11 is a sectional view taken on line 11—11 in FIG. 5.
Figure 5:
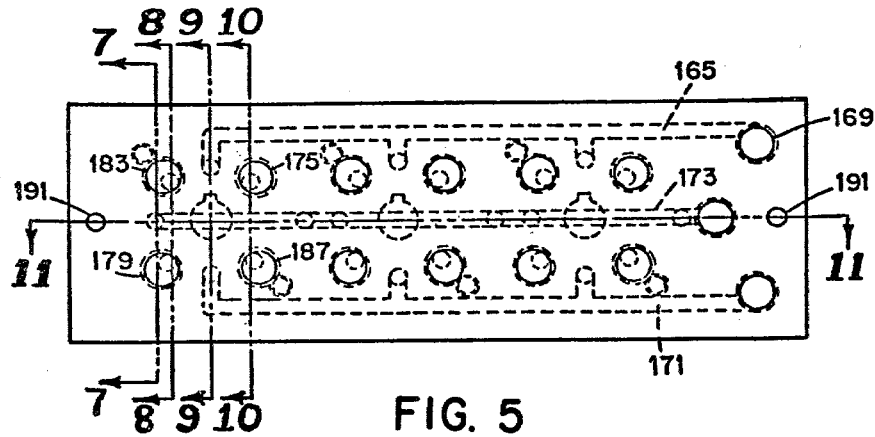
FIG. 5 is a plan view of the assembled manifold shown in FIG. 4.

The valves 25, 25a and 25b are identical so that only one, 25, will be described, the corresponding parts on the valves 25a and 25b will be given the same reference numerals with the suffixes "a" and "b", respectively. Valve 25 includes a base 112 having a mounting face 114 which is adapted to engage the mounting section 109 (FIG. 11) of the manifold 15. Provided in the valve mounting face 114 are a drive air inlet 115, a drive air outlet 117, a chip air inlet 119, a chip air outlet 121, a water inlet 123, a water outlet 125, a pilot air inlet 127 and a pilot air outlet 129. The manifold mounting section 109 is provided with a mounting face 131 which is correspondingly provided with a drive air outlet 133, a drive air inlet 135, a chip air outlet 137, a chip air inlet 139, a water outlet 141, a water inlet 143, a pilot air outlet 145 and a pilot air inlet 147. The inlet and outlets on the mounting face 131 of the mounting section 109 and the mounting face 114 on the valve 25 are arranged in mirror image patterns so that when the valve 25 is mounted, the corresponding inlets and outlets meet. In order to insure proper alignment of the inlets and outlets on the mounting faces 114 and 131, a boss 149 is provided centrally of the mounting face 114 of the valve 25, the boss 149 being provided with a key 151 which engages a keying slot 153 in the pilot air inlet 147 of the mounting face 131.

The middle section 111 of the manifold 15 is provided with a plurality of openings between the mounting section 109 and the face section 113 and otherwise seals the pilot channels 161 formed in the mounting section 109. Opening 133' is positioned to correspond to drive air outlet 133. Opening 135' is positioned to correspond to drive air inlet 135. Opening 137' is positioned to correspond to chip air outlet 137. Opening 139' is positioned to correspond to chip air inlet 139. Opening 143' is positioned to correspond to water inlet 143. Opening 145' is positioned to correspond to pilot air outlet 145.

The face section 113 includes a drive air channel 165 in its inner surface, one end of channel 165 being connected to both a passageway 167 in the mounting section 109 and middle section 111 and a passageway 169 in the face section 113. Passageway 167 is connected to conduit 75. Passageway 169 is connected to conduit 77. The drive air channel underlies only the openings 133', 133a' and 133b' and thus provides communication between the conduit 75 and the drive air valve inlets 115, 115a (not shown) and 115b (not shown).

Also included in the inner surface of the face section 113 is a chip air channel 171, one end of the channel 171 being connected to the chip air inlet 91. The chip air channel 171 underlies only the openings 137', 137a', and 137b' and thus provides communication between the conduit 85 and the chip air valve inlets 119, 119a (not shown) and 119b (not shown).

Also included in the inner surface of the face section 113 is a water channel 173, one end of the channel 173 being connected to the water inlet 99. The water channel 173 underlies only the openings 141', 141a', and 141b' and thus provides communication between the conduit 93 and the water inlets 123, 123a (not shown) and 123b (not shown). Additionally, the face section 113 is provided with a passageway 175 connecting opening 135' to a drive air exit 177, a passageway 179 connecting opening 143' to a water exit 181, a passageway 183 connecting opening 139' to a chip air exit 185 and a passageway 187 connecting a pilot air entrance 189 to opening 145'. The passageways 175, 179, 183 and 187 are preferably threaded to accept a mating threaded nipple for conduit connections.

Extending through all three sections 109, 111 and 113 are a pair of mounting bores 191 for mounting the manifold assembly.

The sections 109, 111 and 113 are preferredly composed of a clear plastic, such as Lexan and sealingly joined by a heat-welding process well known in the art. Clarity of the material allows easy recognition of any obstructions which may by chance develop in the manifold 15.

The base plate 112 of the valve 25 is sealingly engaged against the mounting face 131 of the mounting section 109 of the manifold 15 by means of the mounting screws 157. A suitable gasket (not shown) is preferably interposed between the faces of the base plate 112 of the valve 25 and the mounting face 131 of the mounting section 109 of the manifold 15 to insure a pressure tight connection.

The valve 25 includes an elongated cylindrical housing 193 having an internal, axial, central passageway 195 defined by a cylindrical wall 197. One end of the housing 193 is attached to the base plate 112 and the other end of the housing is provided with an end cap 199 which seals the outer end of the passageway 195. Disposed within the passageway 195 is a spool assembly 200. The spool assembly 200 includes a shaft 201, of relatively small diameter, having an axially extending central opening 203. The shaft 201 also is provided with four, integral, spaced-apart enlargements 204, 205, 206 and 208, each of which has a circular cross section which approaches the diameter of the passageway 195.

Sealing means 207 are provided between each of the enlargements and the side wall 197 of the passageway 195 to divide the passageway into three sealed annular compartments 209, 210 and 212. The sealing means 207 on each of the enlargements 204, 205 and 206 each include a pair of spaced apart seals 207' which provide a sealed chamber 214 of small volume which is isolated from the adjacent compartment. A single seal 207' is provided on the enlargement 208. The seals are desirably provided by O-rings or the like.

The length of the shaft 201 is less than the length of the passageway 195 so that the shaft, with its associated enlargements 204, 205, 206 and 208 can move longitudinally within the passageway 195. A compression spring 211 is disposed in the passageway 195, one end of the spring 211 bearing upon a shoulder 213 on the base plate 112 and the other end of the spring 211 bearing upon the enlargement 208. Thus, the spring 211 normally biases the spool assembly 200 away from the base 112.

In order to move the spool assembly 200 towards the base 112, pilot air (the source of which will be hereinafter described) is conducted from the inlet 127 in the base plate 112, through a passageway 216 in the wall 197 of the housing 193 through an inlet 218 to a space 221 between the cap 199 and the enlargement 204, the enlargement most remote from the base. This builds up air pressure in the space 221 which acts upon a piston surface 223 provided by the enlargement 204 to move the spool assembly 200 towards the base plate 112. It will be noted that the central opening 203 in the shaft 201 is connected through the outlet 129 on the base plate 112 through the channel 161 to the exhaust port 163. In order that pressure builds up in the space 221 between the cap 199 and the enlargement 205, the diameter of the central opening 203 is sufficiently small to provide a back pressure which results in the necessary pressure build-up to overcome the biasing action of the spring 211.

Included within the housing 193 is a passageway 225 connecting the drive air inlet 115 in the base plate 112 to a drive air wall inlet 227, a passageway 228 connecting a drive air wall outlet 229 to the drive air outlet 117 in the base plate 112, a passageway 231 (FIG. 3B) connecting the chip air inlet 119 in the plate to a chip air inlet 233 (FIG. 3B), a passageway 235 connecting a chip air wall outlet 237 to the chip air outlet 121 in the base plate, a passageway 239 connecting the water inlet 123 in the base plate 112 to a water inlet 241 and a passageway 243 connecting a water wall outlet 244 to the water outlet 125 in the base plate.

Figure 3A:
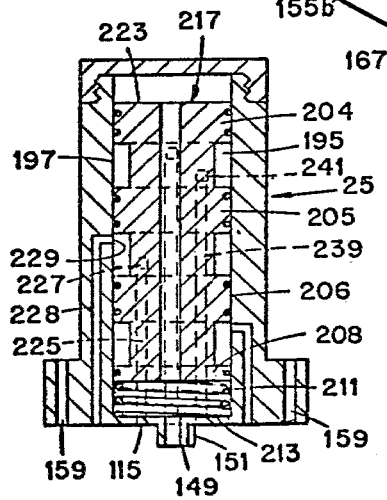
FIG. 3A is a sectional view taken on line 3—3 in FIG. 1 of a replaceable valve assembly unit, the valve being in the open position.
Figure 3B:
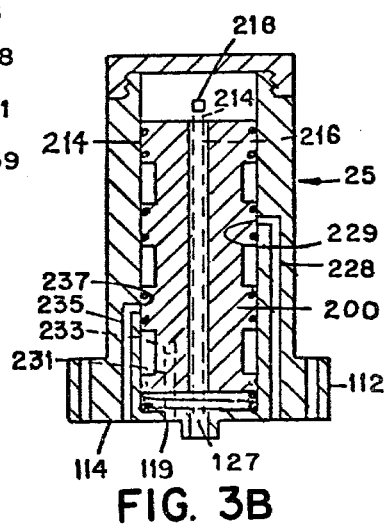
FIG. 3B is a sectional view taken on line 3B—3B in FIG. 1 of a replaceable valve assembly unit, the valve being in the closed position.
Figure 3:
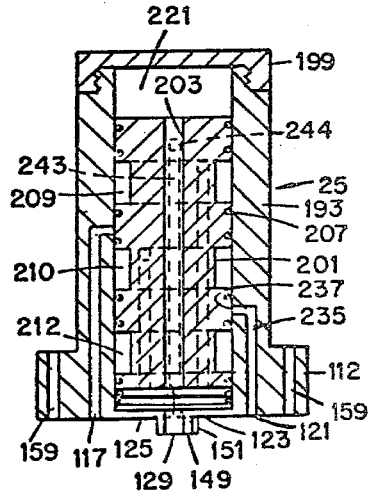
FIG. 3 is a sectional view taken on line 3—3 in FIG. 1 of a replaceable valve assembly unit, the valve being in the closed position.
Figure 6:
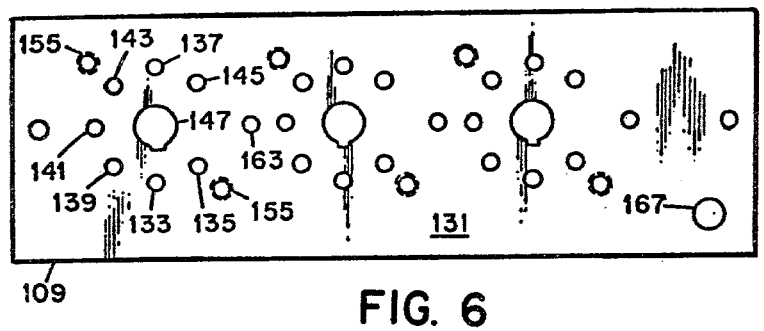
FIG. 6 is a plan view of the face of the manifold shown in FIG. 5 which is adapted to receive the replaceable valve assembly units.
Figure 7:
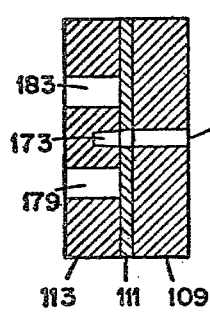
FIG. 7 is a sectional view taken on line 7—7 in FIG. 5.
Figure 8:
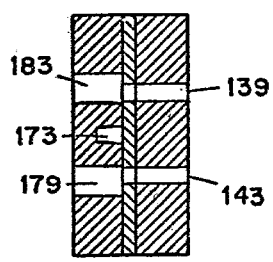
FIG. 8 is a sectional view taken on line 8—8 in FIG. 5.
Figure 9:
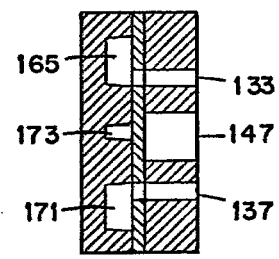
FIG. 9 is sectional view taken on line 9—9 in FIG. 5.
Figure 10:
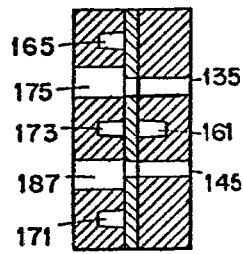
FIG. 10 is a sectional view taken on line 10—10 in FIG. 5.

The wall inlets and wall outlets for drive air, chip air and water described above are positioned along the wall 197 as illustrated in FIGS. 3, 3A and 3B. It will be noted that the drive air wall inlet 227 and wall outlet 229 are spaced along the axis of the passageway 195 a distance such that when the spool 200 is in its position remote from the base plate 112, the inlet 227 and outlet 229 are in communication through the compartment 210. However, when the spool 200 is biased towards the base plate 112 by the action of pilot air the inlet 227 is in communication with the compartment 210 and the outlet 209 is in communication with the chamber on the enlargement 205, thus isolating the inlet and outlet one from the other.

The chip air wall inlet 223 and chip air wall outlet 237 are similarly positioned with respect to compartment 212 and the annular chamber surrounding enlargement 206.

The water inlet 241 and water wall outlet 244 are similarly positioned with respect to compartment 209 and the annular chamber surrounding enlargement 204.

Connected to the drive air outlet 177 is a regulator 255 which may be set to determine the maximum drive air pressure available for a particular tool. As illustrated, conduit 17, which supplies drive air to the drill 13, is connected to the regulator 255. Also connected to the regulator, through conduit 257, is an air gauge 259. Conduit 257 is connected at the distribution box 79 to an internal passageway 261 which is connected to a conduit 262 which connects to the air gauge 259. As shown in FIG. 2, all tool stations are similarly connected to the passageway 261 at the distributor box 79. The air gauge 259 thus provides a visual measure of the pressure of drive air supplied to the tool which is in use.

Also connected to passageway 261 and passageway 81 in the distributor box 79 are conduits 263 and 265, respectively, which are in turn connected to a normally open relief valve 267. Relief valve 267 normally vents to the atmosphere all drive air, chip air and water control air conduits between the foot pedal actuated valve 29 and the valve 25. The relief valve is closed when the foot pedal is activated to allow drive air flow from conduit 73 into conduit 75.

A particularly useful type of valve to use for the air actuated water valve 97 is one which includes an "antisyphon" feature to prohibit dripping after water flow is stopped. Such valves are available commercially.

In operation, the above described system provides a flexible means to control the operation of dental or surgical drills. As has been pointed out, the usual installation includes a plurality of drills or other tools such as the tools 13, 13a, and 13b, as shown in FIG. 2. Each of these tools is adjusted to provide the proper operating speed for a given job by preadjusting the regulators 255, 255a or 255b, as required, and each of the proper bits are placed in each of the tools prior to operating on a patient. In order to supply the system the master valve 43 is turned on supplying drive air, chip air and water or other liquid to the manifold 15, the valve 87, and the valve 97, respectively, in the manner which has been described. The dentist or surgeon then determines whether he will require chip air or water for the operation of the tool and presets this condition through the valve 105 for water and the valve 87 for chip air.

As has been pointed out above, when the unit is in the ready condition, pilot or control air is flowing through each of the spool valves 25, 25a, and 25b to maintain the spool in a position adjacent its respective base plate 112, 112a and 112b, thereby preventing the flow to any of the tools, as shown in FIGS. 3 and 3A. Assuming that the operator chooses to use tool 13, he lifts it from its associated hanger 27 which blocks the flow of control air to only the associated spool valve 25. Control air continues flowing to spool valves 25a and 25b, maintaining their closed positions. As soon as the supply of control air to the valve 25 is interrupted the spring 211 causes the spool to move axially in the passageway 195 which movement simultaneously provides a supply of drive air, and chip air and/or water as selected, to the tool 13 upon actuation of the foot pedal actuated valve 29. When the foot pedal controlling valve 29 is released the supply of drive air, water and chip air to the tool is stopped and the air pressure in the system going to the tool is vented through the relief valve 267. Replacement of the tool 13 back on its hanger 27 causes control air to again flow through the passageway in the spool valve 25, causing the spool to move against the pressure of the spring 211 thereby closing off simultaneously the supply of both air and liquid to the tool. It is obvious that if the capacity of the various conduits is of the proper size, more than one tool can be run at a time. However, in the illustrative embodiment of the invention each tool would be supplied with the same selected combination of chip air and water.

In the event that the system malfunctions in any way it is relatively easy to service. The provision of the transparent manifold makes it possible to visually examine all of the interior passages of the manifold to determine the location of any points at which it may be blocked. Also, the provision of the spool valves 25, which simultaneously control the multiple supplies to each tool may be readily dismounted by removing the mounting screws 157 and replacing the valve unit 25 with another one of the same construction. Since the position of the valve is keyed to a given position on the mounting face of the manifold through the boss 149 and the key 151 it is apparent that there is no possibility for misconnecting any fluid lines. It has been determined that with an integral valve unit and manifold of the type described that the replacement of a valve can be accomplished in but a few minutes thereby insuring that there is a minimal chance of any tool being out of service for more than a short period of time.

Figure 12:
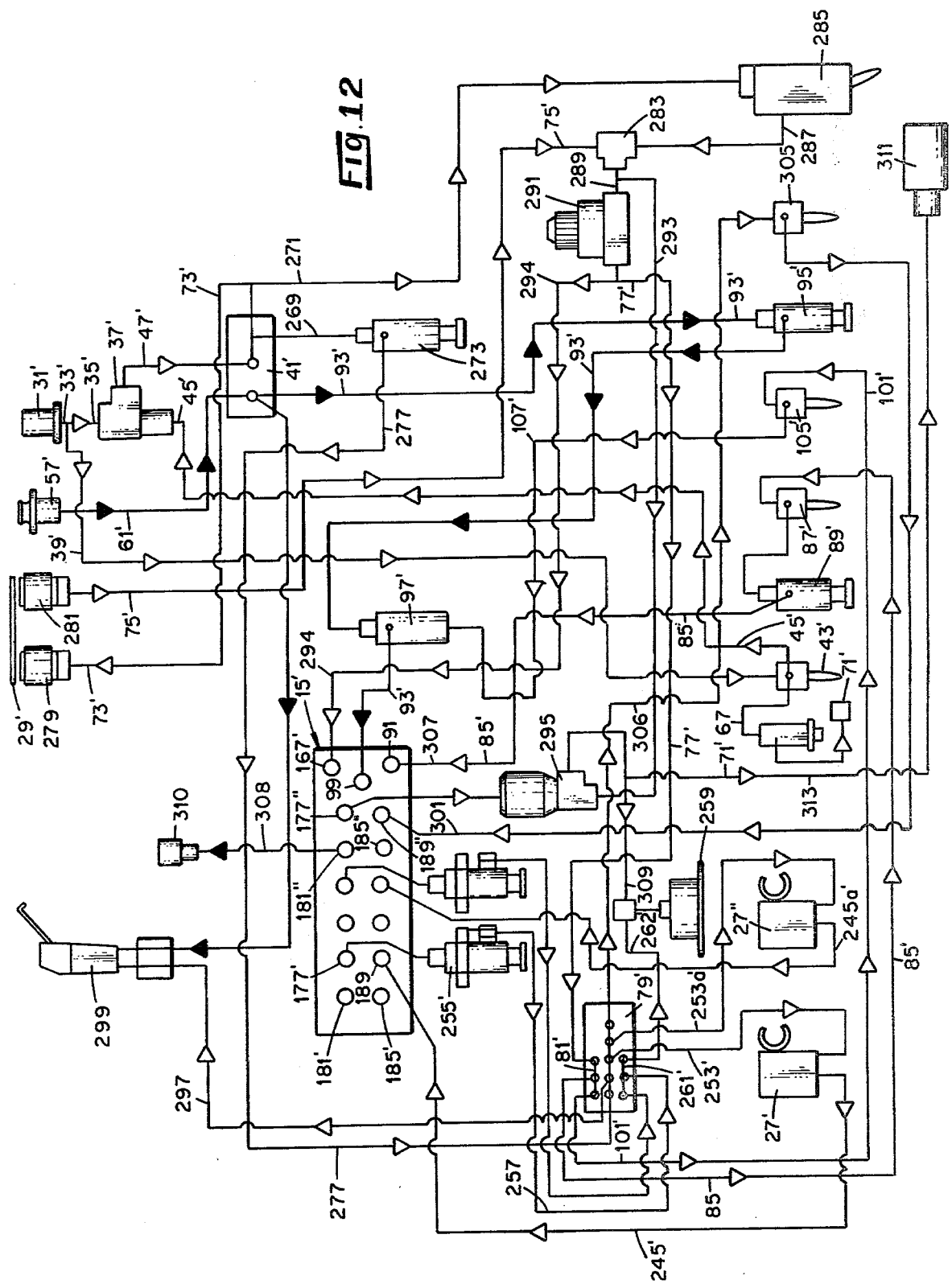
FIG. 12 is a schematic flow diagram of a control system for controlling both low pressure drive gas and high pressure drive gas.

In FIG. 12 there is illustrated a modified system of the type disclosed in the foregoing which is adapted to supply a set of three gas turbine tools, one of which tool comprises a high pressure surgical drill and the remaining tools are conventional drills. In order to simplify the description, only the connections for the high pressure drill and for one of the conventional drills will be described in detail, it being understood that the other conventional drill is connected in a similar manner.

The system shown in FIG. 12 includes many of the features described in connection with the previous embodiment and, in order to simplify the description, the elements which have previously been described will not be described again but will be assigned the same reference numeral with the designation prime ('). The system of FIG. 12 includes a manifold 15' which is adapted to serve three separate tools. The manifold 15' is supplied with low pressure drive gas, chip gas and liquid at working pressures. Control of the flow of fluids from the manifold 15' to each tool is accomplished by an individual self-contained removable spool valve set which is identical to the set which has been previously described in connection with reference numeral 25. In operation, each valve set is actuated by a source of pressurized pilot gas to simultaneously permit flow of the desired combination of drive gas, chip gas and liquid to its associated tool.

In connection with one of the valve sets, the pressurized drive gas is employed to actuate a pressure actuated valve which is adapted to supply high pressure drive gas to the high torque low speed drill. This permits the entire system to operate at lower pressures while isolating the higher pressure system to one tool to enhance safety and to decrease expense.

The system is connected to a suitable source of pressurized gas 31' through conduit 33'. The pressure at the source 31' is selected to a higher pressure than the highest pressure to be supplied to the high pressure tool, taking into account the pressure drop which occurs in the system between the source of gas and the tools, for example 150 psi or even higher. The conduit 33' is connected through the conduit 35' to the inlet of a gas actuated, normally closed control valve 37' and through conduit 39' to a manually actuated master valve 43'. When the master valve 43' is manually opened, it supplies gas through conduit 45' to the gas operated valve 37' which is thus opened connecting the source of gas 31' through conduit 47' to the junction block 41'. In the conduit 47', there may be provided a suitable filter (not shown in FIG. 12) to remove any undesirable suspended material and a regulator to control the pressure of gas supplied to the system (also not shown in FIG. 12).

In order that there is an indicator to show whether or not the unit is being supplied with pressurized gas and water, the outlet of the master valve 43' is also connected by conduit 67' through a pressure regulator 69' to a gas actuated indicator light 71'.

The gas entering the junction box 41' through the conduit 47' exits from the junction box through the three conduits 73', 269 and 271. Conduit 269 is connected to a pilot regulator 273, which receives gas at essentially the source pressure. Gas at a reduced pressure leaves the pilot regulator 273 through conduit 277 to supply pilot gas to the distribution block 79'.

Conduit 73' is connected to one side of the variable foot pedal actuated valve 29' through the plug 279. Gas is returned from the other side of the foot pedal actuated valve through the plug 281 and the conduit 25' to a first inlet of a hand-foot isolation valve 283.

Conduit 271 is connected to a hand-foot switch 285, which is connected to a second inlet of the hand-foot isolation valve 283 by the conduit 287. In the "hand" position, the switch 285 permits gas from conduit 271 to flow directly to the valve 283 without passing through the foot pedal actuated valve 29'. In the "foot" position, gas must pass through the variable foot pedal actuated valve 29' to reach the valve 283.

The outlet of the hand-foot isolation valve 283, is connected through conduit 289 to a low pressure drive air regulator 291 and through conduit 293 to the high pressure drive air inlet of a normally closed relay valve 295.

The low pressure drive gas regulator 291 supplies low pressure drive gas through the conduit 294 to the drive air inlet passageway 167' in the manifold 15' at a pressure at least as great as that pressure required to drive the conventional low pressure drive gas tools.

In order to provide a source of chip gas, a conduit 77' which communicates with the conduit 76, extends to the distribution block 79'. The distribution block 79' includes an internal passageway 81' which is connected by means of a conduit 85' through a manually operated valve 87', which determines whether or not chip gas is to be supplied to the system, through a gas regulator 89' to the chip gas inlet 91' on the manifold 15' by means of conduits 85'.

In order to supply water to the manifold 15', the conduit 61' connects the source of water 57' to the junction block 41' which in turn is connected by means of conduit 93' including a pressure regulator 95' and a gas actuated valve 97' to the water inlet 99 on the manifold 15'. Control of the supply of water is effected by the gas actuated valve 97'. This control is effected by gas from a gas conduit 101', having one end connected to the passageway 81' in the distribution block 79'. The other end of the conduit 101' is connected to the inlet of a manually actuated gas valve 105' whose outlet communicates with the gas inlet on the control valve 97' through the conduit 107'.

Pilot air supplied to the distribution block 79' through the conduit 277 is directed through the conduit 253 as pilot air to the hanger 27', then through the conduit 245 to the pilot air inlet 189' in the manifold 15'. Pilot air from the conduit 277 is also distributed through the conduit 297 to a syringe 299 to activate its water supply. The positions on the manifold 15' for the high pressure drill control are as follows: 177" is the outlet for low-pressure drive air; 181" is the outlet opening for water; 185" is the outlet for chip air (which opening is blocked because chip air is not normally employed with high pressure-high torque tools); and 189" is the inlet for pilot air for the high pressure unit. Pilot air is conducted to the inlet 189" through conduit 301.

A manually operable air switch 305 is connected to the other end of the conduit 301 to control pilot air flow to the inlet 189" from the distribution block 79' through the conduit 306. Alternatively, a hanger (not shown) may be provided for the high pressure drill to control pilot air. It is desirable, however, to use the switch 305 to ensure that the operator has made a deliberate decision to use the high pressure drill.

A conduit 307 connects the drive air outlet 177" of the manifold 15' to the control inlet of the relay valve 295. The high pressure drive air outlet of the relay valve 295 is connected to the gauge 259 by the conduit 309 and to the high pressure outlet plug 311 by the conduit 313. The high pressure outlet plug 311 is connected to the high pressure tool to provide its driving air.

Connected to the drive gas outlet 177' for low pressure drive gas is a regulator 255' which may be set to determine the maximum drive gas pressure available for its associated low pressure drive gas tool. The gauge 259' is also connected to the regulator 255', through conduit 257' and the distribution box 79' whose internal passageway 261' is connected to a conduit 262' which in turn connects to the gauge 259'. As shown in FIG. 12, all tool stations are similarly connected to the passageway 261 at the distribution box 79'. The gauge 259' thus provides a visual measure of the pressure of drive gas supplied to the tool which is in use.

In operation, the master switch 43' is opened to permit gas flow (at a pressure greater than that pressure required to run a high pressure drill) to the pilot regulator 273, the foot pedal actuated valve 29' and the hand-foot switch 285. If a foot-operated drill is to be used, the hand-foot switch 285 is placed in the "foot" position, thus barring flow through the conduit 287. As the foot pedal actuated valve 29' is normally closed, no gas flows through the conduit 75.

From the pilot regulator 273, gas flows at the desired reduced pressure through conduit 277 to the distribution block 79'.

At the distribution block 79', the gas flowing through conduit 277 is split to supply gas to activate the closed syringe 299, pilot gas to the normally open individual hanger switches 27' and 27" and pilot gas to the normally open individual manual witch 305. From the individual switches, the pilot gas is directed through the conduits 245, 245a and 301 to the pilot gas inlet 189 etc. for each valve set 25 on the manifold. The pilot gas flows through the passageways of the manifold to maintain the spool valves in a normally closed position and then is released to the atmosphere.

When the operator chooses to use a low pressure drive gas tool, he lifts it from its associated hanger 27, thus blocking the flow of pilot gas to only the associated spool valve. Control gas continues flowing to the spool valves associated with the other hanger switch 27'' and the manual switch 305, thus maintaining their closed positions.

As the foot pedal actuated valve 29' is opened, gas flows through the conduit 75 through the hand-foot isolation valve 283 to the low pressure drive gas regulator 291. From the regulator 291, the gas, at a substantially reduced pressure, is conducted to the conduit 81' in the distribution block 79' and to the drive gas inlet 167' in the manifold 15'.

From the conduit 81' in the distribution block 79', the gas is directed through conduits 85 and 101 to the chip gas switch 87' and the liquid control switch 105', respectively. Then, as selected by the operator, chip gas flows to the chip gas inlet 91' in the manifold 15' and gas flows to actuate the liquid valve 97', permitting liquid flow to the liquid inlet 99' in the manifold 15'. As described above, common passages in the manifold distribute low pressure drive gas, chip gas and liquid to the individual spool valves. The selected fluids and low pressure drive gas flow through the open valve and through low pressure individual passageways in the manifold to the drive gas outlet 177, then through conduits to the selected tool until the foot pedal actuated valve is again closed.

When the operator chooses to use the high pressure tool, the switch 305 is closed, halting the flow of pilot gas to the inlet 189'' and thus opening its associated spool valve. Thereafter, as the foot pedal is depressed and gas flows through the conduit 75, it is directed to the low pressure drive gas outlet 177'' as well as the high pressure inlet of the relay valve 295. Low pressure drive gas exiting from the outlet 177'' through conduit 307 opens the relay valve 295, permitting high pressure drive gas to flow through the conduit 313 to the plug 311 which is attached to the drive air inlet of the high pressure tool.

When the high pressure tool is actuated liquid is simultaneously conducted to the tool through liquid outlet 181'', conduit 308 and plug 310 which is connected to the tool (as noted above, chip air is normally not employed with the high pressure drill, but if it is it can be supplied through outlet 185'' in the manifold 15').

In those situations in which the tool to be used includes a hand control, the hand-foot switch 285 is placed in the "hand" position, permitting high pressure gas to flow directly to the relay valve and low pressure gas to flow directly to the low pressure drive gas inlet 91, the chip gas switch 87 and the liquid switch 105.

The system described herein permits a single pressurized gas source to be used to supply several tools. However, the entire system does not require the reinforcement for handling the substantially greater pressures, nor are large number of regulators required to reduce pressures for various different uses for gas in the system.

While a preferred embodiment has been shown and described, it will be understood that there is no intent to limit the invention by such disclosure, but rather, it is intended to cover all modifications and alternate constructions falling within the spirit and scope of the invention as defined in the appended claims.

What is claimed:

1. A system for providing pressurized gas from a single pressurized gas source to a plurality of gas-powered tools, including at least one high pressure tool requiring gas at a substantially greater pressure than the pressure required for the remaining conventional tools, comprising conduit means connecting said gas source to a pilot gas regulator, individual conduit means connecting said pilot gas regulator to a plurality of individual switches, each one of said individual conduit means connecting each of said switches to a control air inlet of one of a plurality of actuating valves, each actuating valve being associated with one of said tools, conduit means connecting said gas source to a low pressure drive gas regulator, low pressure drive gas conduit means connecting said low pressure drive gas regulator to each of said actuating valves, conduit means connecting said actuating valves associated with said conventional tools to said conventional tools, conduit means connecting said pressurized gas source to a high pressure inlet of a relay valve, conduit means connecting the drive gas outlet of the actuating valve associated with said high pressure tool to a low pressure inlet of said relay valve and conduit means connecting a high pressure outlet of said relay valve to said high pressure tool, whereby pilot gas flow to each individual actuating valve actuates low pressure drive gas flow from each of said valve and low pressure drive gas flow from said equivalent valve associated with said high pressure tool to said relay valve actuates high pressure drive gas flow to said high pressure tool.

2. A system as described in claim 1 wherein said actuating valves comprise self-contained spool valves mounted upon a unitary manifold.

3. A system as described in claim 1 wherein said conduit means connecting said pressurized gas source to said low pressure drive air regulator and said conduit means from said pressurized gas source to said high pressure inlet of said relay comprise common conduit means from said pressurized gas source to an isolator valve and said common conduit means comprise a first alternative conduit including a variable foot control valve and a second alternative conduit including a hand-foot actuated switch.

4. A system as described in claim 1 wherein said individual switches associated with said remaining tools comprise hanger switches and said individual switch associated with said high pressure tool comprises a manually operable switch.

5. A system as described in claim 1 wherein an individual regulator is disposed within each individual conduit connecting said equivalent valves associated with a conventional tool to the associated conventional tools.

* * * * *

UNITED STATES PATENT OFFICE
CERTIFICATE OF CORRECTION

Patent No. 4,201,051  Dated May 6, 1980

Inventor(s) Arthur L. Hall

It is certified that error appears in the above-identified patent and that said Letters Patent are hereby corrected as shown below:

Column 2, line 60, change "explosives" to --explosions--.

Column 6, line 48, after "water" insert --wall--.

Column 6, line 65, change "223" to --233--.

Column 9, line 28, change " 25' " to --75'--.

Column 10, line 60, change "witch" to --switch--.

Column 12, line 42, after "foot" insert --actuated--.

Signed and Sealed this

Fifteenth Day of July 1980

[SEAL]

Attest:

Attesting Officer

SIDNEY A. DIAMOND

Commissioner of Patents and Trademarks